(12) United States Patent
Hebrard et al.

(10) Patent No.: US 9,072,487 B2
(45) Date of Patent: Jul. 7, 2015

(54) ULTRASOUND PROBE THERMAL DRAIN

(75) Inventors: Jean Marc Hebrard, Sophia Antipolis (FR); Daniel Vignet, Sophia Antipolis (FR)

(73) Assignee: General Electric Company, Schenectady, NY (US)

( * ) Notice: Subject to any disclaimer, the term of this patent is extended or adjusted under 35 U.S.C. 154(b) by 532 days.

(21) Appl. No.: 13/469,312

(22) Filed: May 11, 2012

(65) Prior Publication Data

US 2013/0301395 A1 Nov. 14, 2013

(51) Int. Cl.
*A61B 8/00* (2006.01)
*G01S 7/52* (2006.01)
*B06B 1/06* (2006.01)

(52) U.S. Cl.
CPC ............. *A61B 8/4455* (2013.01); *B06B 1/0622* (2013.01); *G01S 7/52079* (2013.01); *A61B 8/546* (2013.01)

(58) Field of Classification Search
CPC .............................. B06B 1/0622; A61B 8/546
USPC ........................ 600/459; 216/13, 20; 367/189
See application file for complete search history.

(56) References Cited

U.S. PATENT DOCUMENTS

| 5,721,463 | A | 2/1998 | Snyder | |
|---|---|---|---|---|
| 8,084,923 | B2* | 12/2011 | Guo | 310/334 |
| 2006/0100513 | A1 | 5/2006 | Hashimoto | |
| 2008/0195003 | A1* | 8/2008 | Sliwa et al. | 601/3 |
| 2008/0262358 | A1* | 10/2008 | Kaminski et al. | 600/459 |
| 2010/0231093 | A1 | 9/2010 | Li | |
| 2011/0114303 | A1* | 5/2011 | Rhim | 165/185 |
| 2012/0143060 | A1 | 6/2012 | Weekamp et al. | 600/459 |
| 2013/0145611 | A1* | 6/2013 | Guo | 29/594 |
| 2013/0301395 | A1* | 11/2013 | Hebrard et al. | 367/189 |

* cited by examiner

*Primary Examiner* — Mark Hellner
(74) *Attorney, Agent, or Firm* — Rathe Lindenbaum LLP (57) ABSTRACT

An ultrasound probe includes a thermal drain across which heat is thermally conducted from an ultrasound transducer to an outer polymeric casing wall of the ultrasound probe.

20 Claims, 13 Drawing Sheets

ULTRASOUND PROBE THERMAL DRAIN

BACKGROUND

Ultrasound or ultrasonography is a medical imaging technique that utilizes high-frequency (ultrasound) waves and their reflections. Such ultrasound waves are directed into a person's anatomy using a handheld probe. Current ultrasound probes typically limit the ultrasound waves directed into the person's anatomy to satisfy surface temperature regulations for the ultrasound probe. The limiting of ultrasound waves directed into a person's anatomy may also result in lower ultrasound imaging quality.

DETAILED DESCRIPTION OF THE EXAMPLE EMBODIMENTS

Figure 1:
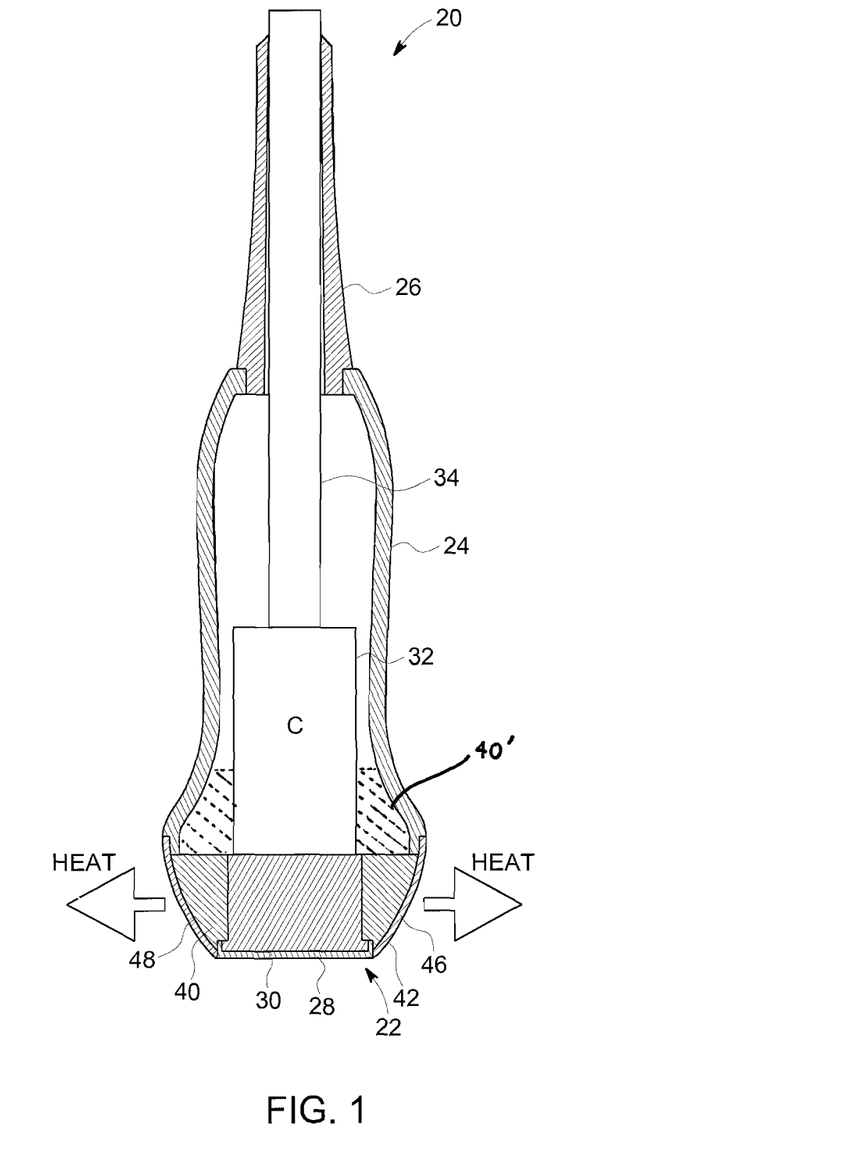
FIG. 1 is a sectional view schematically illustrating an example ultrasound probe with a thermal drain.

FIG. 1 is a sectional view illustrating an example ultrasound probe 20. As will be described hereafter, ultrasound probe 20 is configured to better dissipate heat produced by an ultrasound transducer so as to allow the use of additional ultrasound energy to enhance ultrasound imaging quality while still satisfying temperature regulations for the ultrasound probe. Ultrasound probe 20 comprises nose 22, main body 24, sleeve 26, lens 28, ultrasound transducer 30, controller 32, power-communication cable 34 and thermal drain 40.

Nose 22 extends at a forward end of probe 20 so as to at least partially enclose and support lens 28 and transducer 30. Nose 22 comprises an outer polymeric casing wall 42 which extends about lens 28 and is in thermal contact with thermal drain 40. Casing wall 42 relies upon thermal drain 40 for structural support such that casing wall 42 has a reduced thickness of no greater than 3 mm, nominally less than 1 mm and nominally less than 0.6 mm. As a result, casing wall 42 has a lower thermal resistance such that heat produced by transducer 30 may be more uniformly, continuously and effectively dissipated. In one implementation, case law 42 is formed from a flame retardant polybutylene terephthalate (PBT) such as Valox 357 PBT commercially available from SABIC Innovative Plastics. In other implementations, other polymers may be utilized for casing wall 42.

Body 24 comprises a tubular structure extending rearward from nose 42. Body 24 supports nose 42 while enclosing controller 32 and cable 34. Body 24 provides a structure by which a person may manually grip and manipulate probe 20. In other implementations, depending upon what portion of an anatomy for which ultrasound probe 20 is to be used, body 24 may have other sizes, shapes and configurations.

Sleeve 26 extends rearwardly from body 24 to guide and receive cable 34. Sleeve 26 serves as a strain relief to relieve strain during flexing or bending of cable 34 as a result of manipulation of ultrasound probe 20. In other implementations, sleeve 26 may be omitted. For example, in other implementations, ultrasound probe 20 may communicate with external display devices are external analysis devices in a wireless fashion using a wireless antenna contained within body 24. In such an implementation, power maybes supplied to also probe 20 using a rechargeable battery. In such an implementation, sleeve 26 may be omitted.

Lens 28 comprises an acoustic lens located at an end of nose 42 to focus emitted sound waves. Although illustrated as being a generally a linear cylinder, in other implementations, lens 28 may have other configurations. For example, lens 28 may alternatively be a curved cylinder such as in implementations where probe 20 comprises an abdominal probe or where probe 20 comprises an endocavity probe.

Transducer 30 comprises an ultrasound device located at a front end or nose 22 of probe 20 that is configured to emit and receive sound waves (ultrasonic waves). During imaging by probe 20, the nose 22 of probe 20 may be placed upon or against the exterior of anatomy, or may be partially inserted into anatomy depending upon those portions of the anatomy which are to be imaged. In one implementation, transducer 30 comprises piezoelectric crystals and ceramic, that change shape in response to the application electrical pulse so as to produce vibrations or sound waves. Likewise, the impact of sound or pressure waves upon such crystals produce electrical currents. As a result, such crystals are used to send and receive sound waves. Transducer 30 may additionally include a sound absorbing substance to eliminate back reflections from the probe itself and an acoustic lens to focus emitted sound waves.

Controller 32 comprises an electronic device configured to control operation of ultrasound probe 20. For example, controller 32 may generate control signals controlling and directing emission of ultrasound waves by transducer 30. Controller 32 may additionally facilitate the supply of power to transducer 30 as well as the transmission of signals from ultrasound probe to an external computing device for analysis and display. In one implementation, controller 32 may comprise a printed circuit board supporting one or more electronic components, such as electrical tuning components, communication components and other components for carrying out such functions. In other implementations, controller 32 may comprise an application-specific integrated circuit (ASIC) supported on a printed circuit board. In another implementation, controller 32 may comprise one or more processing units and an associated memory, wherein the one or more processing units follow instructions contained in the associated non-transitory computer-readable medium of the memory to perform or carry out such functions as the supply of power to transducer 30, the control of the emission of ultrasound waves by transducer 30 and the transmission of signals representing sensed ultrasound reflections from the anatomy.

Cable 34 comprises an elongate cable connected to controller 32 to supply power to ultrasound probe 20, to transmit control signals from an external source to controller 34 for the control of transducer 30 and to transmit data signals from ultrasound probe 22 to an external display or analysis system. As noted above, in other implementations, cable 34 may be omitted where such external communication is performed in a wireless fashion and where power is supplied by a battery, such as a rechargeable battery. In such an implementation, body 24 may be slightly reconfigured to facilitate insertion or replacement of the battery.

Thermal drain 40 comprises one or more structures physically located between and in thermal contact with transducer 30 and casing wall 42 so as to thermally couple the transducer 30 to the casing wall 42, wherein the one or more structures of thermal drain 40 are formed from one or more materials having a thermal resistance less than a thermal resistance of the polymeric material forming casing wall 42. For purposes of this disclosure, two members are "thermally coupled" when one or more intermediate heat conducting structures form a bridge or a series of structures, wherein the bridge or series is in contact with the two members and continuously extending between the two members to conduct heat between the two members. In one implementation, thermal drain 40 has a thermal conductivity of at least 150 watts per meter kelvin (W/(m·K)). In one implementation, thermal drain 40 comprises a metal, such as aluminum. In other implementations, thermal drain 40 may comprise other metals or other materials having thermal resistivity is less than that of the polymeric material of outer casing wall 42. In addition to structurally backing and strengthening casing wall 42 such a case wall 42 may be formed with a reduced thickness, thermal drain 40 thermally conducts heat from transducer 30 towards casing wall 42 for enhanced heat dissipation from probe 20. Because heat is continuously and uniformly dissipated away from transducer 30, across thermal drain 40 and through the thinner casing wall 42, surface temperature regulations for the ultrasound probe may be more easily satisfied. As a result, additional energy may be directed into a patient's anatomy by probe 20 for enhanced image quality while still satisfying surface temperature regulations.

In one implementation, thermal drain 40 comprises an insert positioned and held within casing wall 42 of nose 22. In another implementation, thermal drain 40 comprises a structure against which and about which casing wall 42 is over molded. Such over molding facilitates greater surface area contact along an interface between drain 40 and wall 42 for enhanced thermal conduction from drain 40 to wall 42. In one implementation, thermal drain 40 comprises an array of radial fins or baffles extending outwardly from transducer 30 to wall 42. In another implementation, thermal drain 40 comprises a substantially solid structure filling in all volume or space between transducer 30 and wall 42. In one implementation, wall 42 has an interior surface configuration 46 that has a shape and size to identically match or substantially identically match an exterior surface configuration 48 of thermal drain 40 to provide an enhanced thermal interface between drain 40 and wall 46. Although thermal drain 40 is illustrated as being contained within nose 22, as shown by broken lines, in other implementations, probe 20 may alternatively include a thermal drain 40' that is the same as thermal drain 40, except that it additionally extends upward from nose 22 into body 24 (i.e., into the handle or gripping portion of probe 20). With such an implementation, thermal drain 40' may offer enhanced thermal dissipation due to the larger overall mass and overall surface area of thermal drain 40' providing a lower thermal resistance and greater surface area to dissipate heat.

Figure 2:
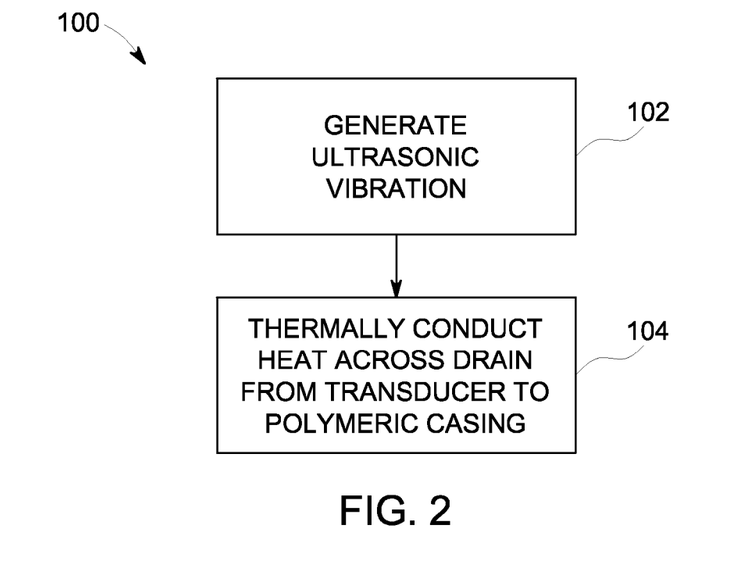
FIG. 2 is a flow diagram of an example method that may be carried out by the ultrasound probe of FIG. 1.

FIG. 2 is a flow diagram illustrating an example method 100 of operation of ultrasound transducer 20. As indicated by step 102, controller 32 generates control signals causing ultrasonic vibrations to be generated by transducer 30. Such vibrations are acoustically focused by lens 28 and are also generating heat. As indicated by step 104, the heat generated by transducer 30 is thermally conducted across thermal drain 40 to polymeric casing wall 42. Because thermal drain 40 not only has an enhanced thermal conductivity as compared to wall 42 but also facilities formation of wall 42 with a reduced thickness, thermal dissipation is enhanced. As a result, greater ultrasound energy may be directed into a person's anatomy for enhanced imaging performance.

Figure 3:
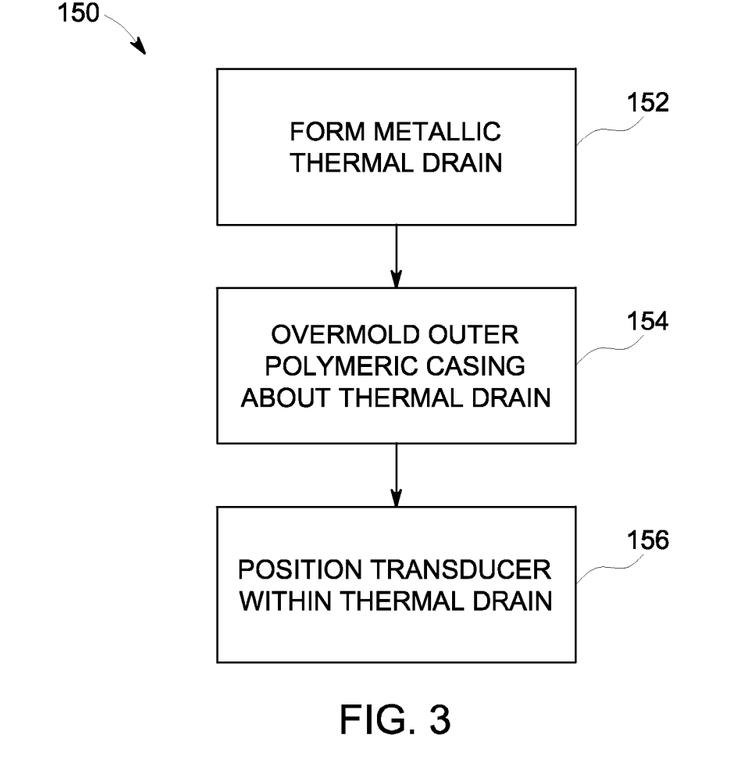
FIG. 3 is a flow diagram of an example method for constructing the ultrasound probe of FIG. 1.
Figure 4:
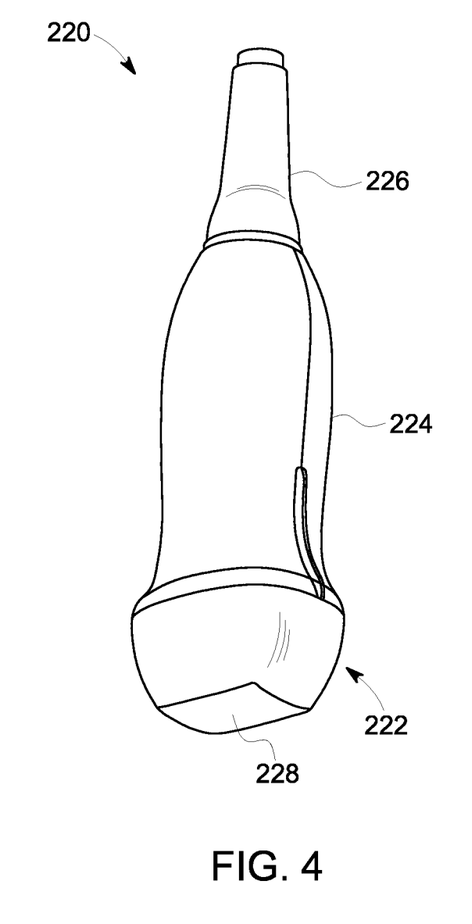
FIG. 4 is a perspective view of an example implementation of the ultrasound probe of FIG. 1.

FIG. 3 is a flow diagram illustrating an example method 150 for forming ultrasound probe 20. As indicated by step 152, thermal drain 40 is initially formed from a metallic material. In one implementation, thermal drain 40 may be formed with a casting or injection molding process. In other implementations, thermal drain 40 may be formed in other fashions.

As indicated by step 154, outer polymeric casing wall 42 is formed by over molding one or more polymeric materials about and onto external surfaces of thermal drain 40. As a result, interior surfaces of casing wall 42 identically match the exterior surface configuration of thermal drain 40 for intimate abutting contact between drain 40 and wall 42. The enhanced surface area contact along the interface between thermal drain 40 and wall 42 provides enhanced thermal conduction and thermal dissipation.

As indicated by step 156, transducer 30 is positioned within thermal drain 40. In one implementation, transducer 30 is positioned within thermal drain 40 after wall 42 has been over molded against and about thermal drain 40. Thereafter, ultrasound probe 20 may be completed with the addition of lens 28 and the remaining components of ultrasound probe 20 shown in FIG. 1.

Figure 5:
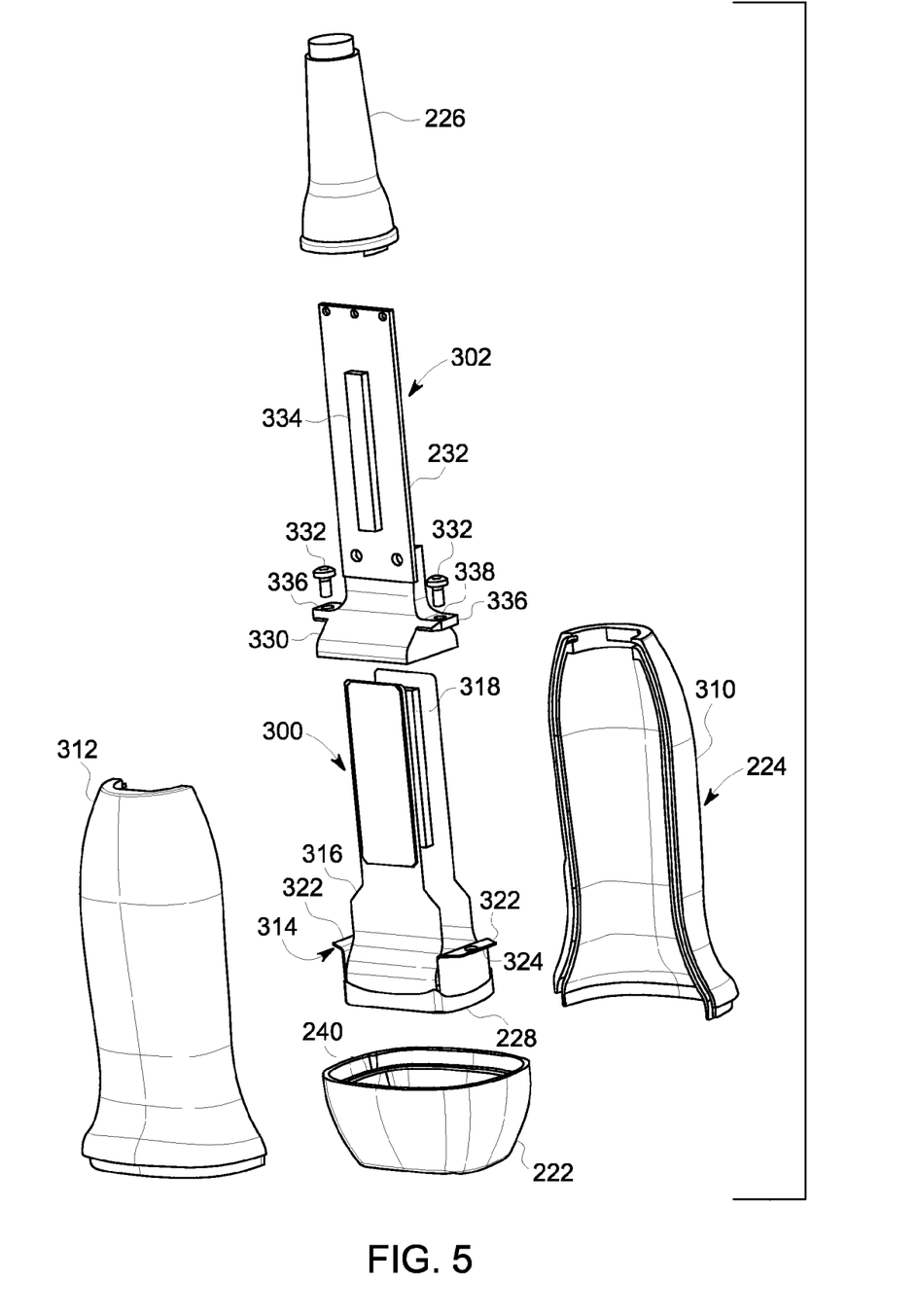
FIG. 5 is an exploded perspective view of the ultrasound probe of FIG. 4.
Figure 6:
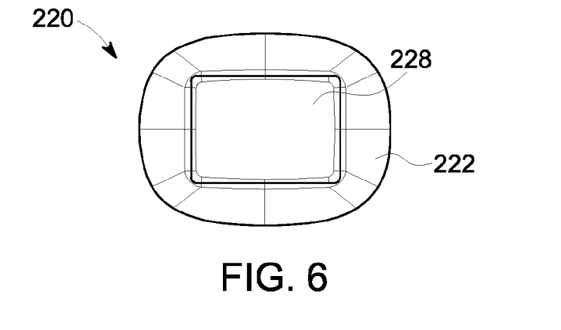
FIG. 6 is a bottom view of the ultrasound probe of FIG. 4.

FIGS. 4-8 illustrate ultrasound probe 220, an example implementation of ultrasound probe 20. As shown by FIG. 5, ultrasound probe 220 comprises nose 222, main body 224, sleeve 226, lens 228, transducer assembly 300 including ultrasound transducer 230 (shown in FIGS. 7 and 8), and controller assembly 302 including controller 232, power-communication cable 34 (shown in FIG. 1) and thermal drain 240.

Nose 222 extends at a forward end of probe 220 so as to at least partially enclose and support lens 228 and transducer 230. Nose 222 comprises an outer polymeric casing wall 242 which extends about lens 228 and is in thermal contact with thermal drain 240. Casing wall 242 relies upon thermal drain 240 for structural support such a casing wall 242 has a reduced thickness of no greater than 3 mm, and nominally less than 1 mm, preferably less than 0.6 mm. As a result, casing wall 242 has a lower thermal resistance such that heat produced by transducer 230 may be more uniformly, continuously and effectively dissipated. In one implementation, casing wall 42 is formed from a flame retardant polybutylene terephthalate (PBT) such as Valox 357 PBT commercially available from SABIC Innovative Plastics. In other implementations, other polymers may be utilized for casing wall 242.

Body 224 comprises a tubular structure extending rearward from nose 242. Body 224 supports nose 242 while enclosing transducer assembly 300 and controller assembly 302. Body 224 provides a structure by which a person may manually grip and manipulate probe 20. In the example illustrated, body 224 is formed from two halves 310, 312 which are joined to one another about transducer assembly 300 and controller assembly 302. In other implementations, depending upon what portion of an anatomy for which ultrasound probe 220 is to be used, body 224 may be formed as a single integral unitary body or may have other sizes, shapes and configurations.

Sleeve 226 extends rearwardly from body 224 to guide and receive cable 234. Sleeve 226 serves as a strain relief to relieve strain during flexing or bending of cable 34 as a result of manipulation of ultrasound probe 220. In other implementations, sleeve 26 may be omitted. For example, in other implementations, ultrasound probe 220 may communicate with external display devices or external analysis devices in a wireless fashion using a wireless antenna contained within body 224. In such an implementation, power maybes supplied to also probe 220 using a rechargeable battery. In such an implementation, sleeve 226 may be omitted.

Lens 228 comprises an acoustic lens located at an end of nose 242 to focus emitted sound waves. Although illustrated as being a generally linear cylinder, in other implementations, lens 228 may have other configurations. For example, lens 228 may alternatively be a curved cylinder such as in implementations where probe 220 comprises an abdominal probe or where probe 220 comprises an endocavity probe.

Transducer assembly 300 provides transducer 230 and facilitates communication between transducer 230 and controller 232. In addition to transducer 230, transducer assembly 300 comprises transducer support 314, flexible circuit 316 and connectors 318.

Figure 7:
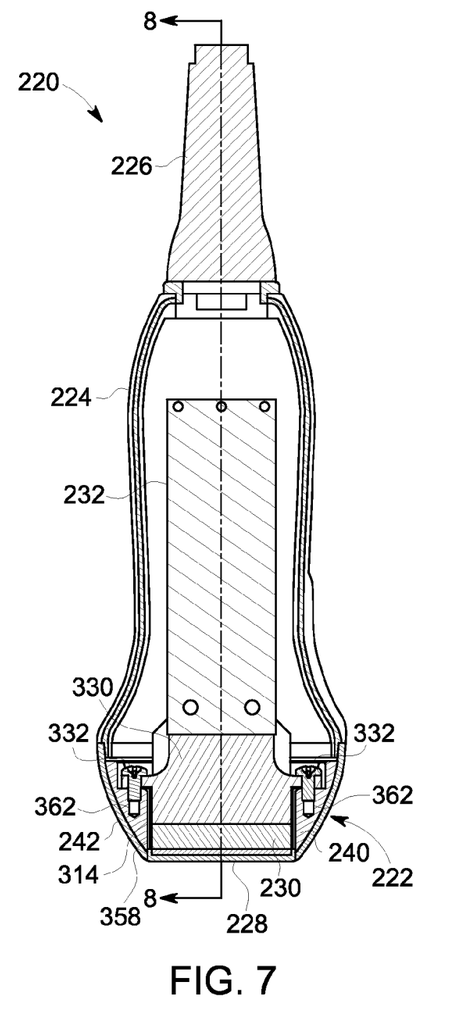
FIG. 7 is a sectional view of the ultrasound probe of FIG. 4.
Figure 8:
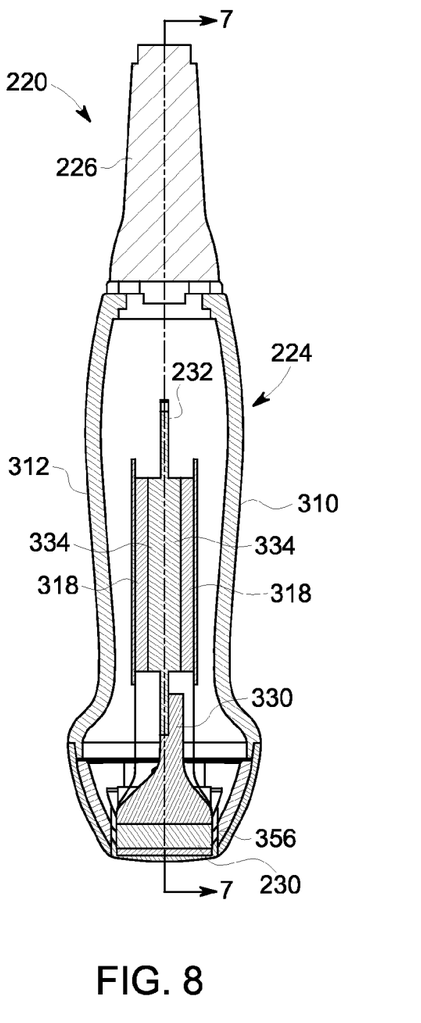
FIG. 8 is a sectional view of the ultrasound probe of FIG. 4 taken along line 8-8 of FIG. 7.
Figure 9:
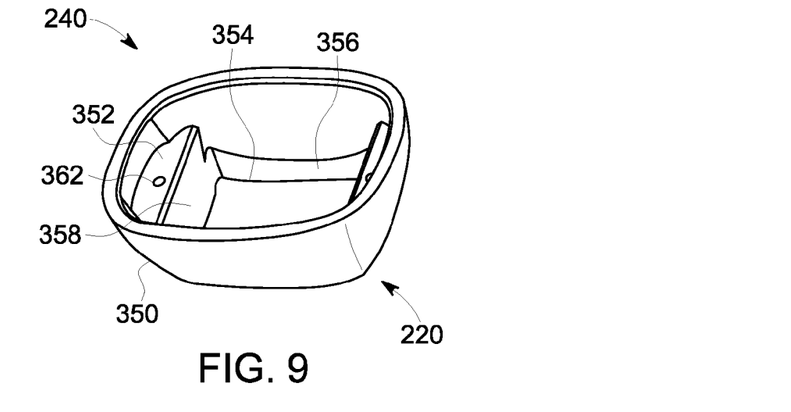
FIG. 9 is a top perspective view of an example thermal drain of the ultrasound probe of FIG. 4.
Figure 10:
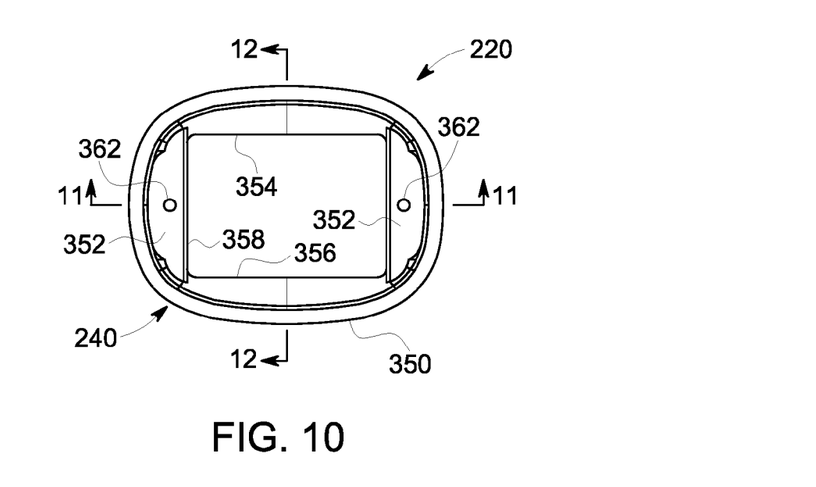
FIG. 10 is a top view of the thermal drain of FIG. 9.
Figure 11:
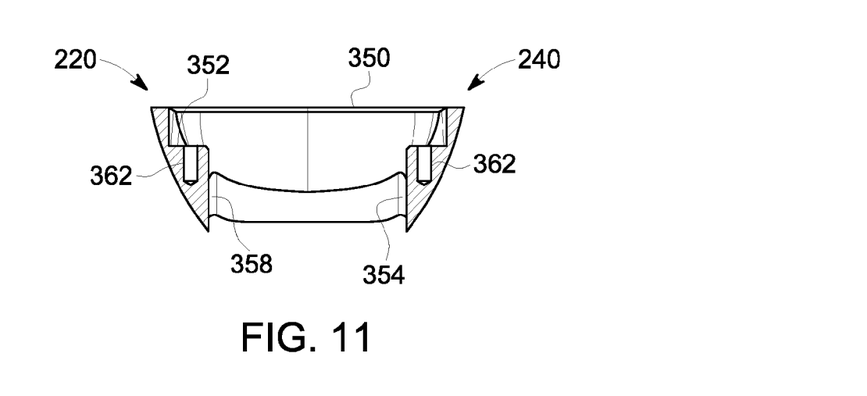
FIG. 11 is a sectional view of the thermal drain of FIG. 9 taken along line 11-11.
Figure 12:
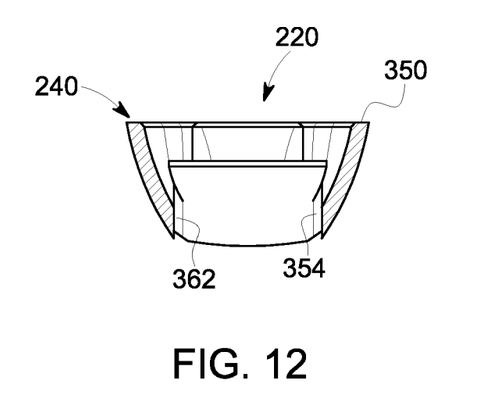
FIG. 12 is a sectional view of the thermal drain of FIG. 9 taken along line 12-12.
Figure 13:
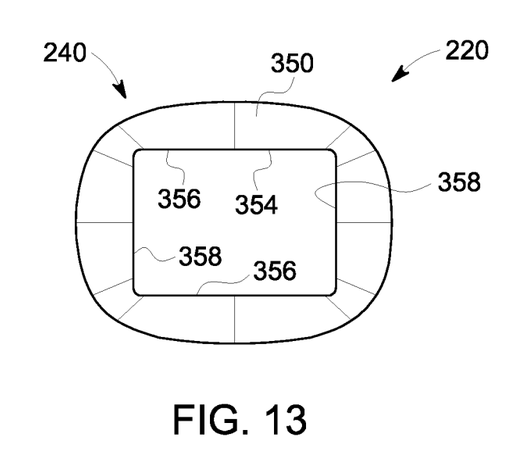
FIG. 13 is a bottom view of the thermal drain of FIG. 9.

Transducer 230 comprises an ultrasound device located at a front end or nose 222 of probe 220 that is configured to emit and receive high-frequency sound waves (ultrasonic waves). In one implementation, transducer 230 comprises a transducer stack. During imaging by probe 220, the nose 222 of probe 220 may be placed upon or against the exterior of anatomy, or may be partially inserted into anatomy depending upon those portions of the anatomy which are to be imaged. In one implementation, transducer 230 comprises piezoelectric crystals or ceramic, that change shape in response to the application electrical pulse so as to produce vibrations or sound waves. Likewise, the impact of sound or pressure waves upon such crystals produce electrical currents. As a result, such crystals are used to send and receive sound waves. Transducer 230 may additionally include a sound absorbing substance to eliminate back reflections from the probe itself and an acoustic lens to focus emitted sound waves.

Transducer support 314 comprises one or more structures that retain support transducer 230 in place with respect to nose 222. In the example illustrated, transducer support 314 comprise a thin metallic foil wrapped about transducer 230 and terminating at opposite ears 322 having apertures 324 facilitating securement of transducer assembly 300 to controller assembly 302. Flexible circuit 316 comprises a flexible circuit containing electrical traces which are connected to transducer 230, wherein flexible circuit 316 extends upward from transducer 230 to connectors 318 which facilitate data communication and the transmission of power between controller 232 and transducer 230. In other implementations, flexible circuit 316 may be omitted in favor of a printed circuit board, cabling, wiring and the like.

Controller assembly 302 supports controller 232 and mounts controller 232 to transducer assembly 300. In addition to controller 232, controller assembly 302 additionally comprises controller mount 330, fasteners 332 and connectors 334.

Controller 232 comprises an electronic device configured to control operation of ultrasound probe 220. For example, controller 232 may generate control signals controlling and directing emission of ultrasound waves by transducer 230. Controller 232 may additionally facilitate the supply of power to transducer 230 as well as the transmission of signals from ultrasound probe to an external computing device for analysis and display. In one implementation, controller 32 may comprise a printed circuit board supporting one or more electronic components, such as electrical tuning components, communication components and other components for carrying out such functions. In other implementations, controller 232 may comprise an application-specific integrated circuit (ASIC) supported on a printed circuit board. In another implementation, controller 232 may comprise one or more processing units and an associated memory, wherein the one or more processing units follow instructions contained in the associated non-transitory computer-readable medium of the memory to perform or carry out such functions as the supply of power to transducer 230, the control of the emission of ultrasound waves by transducer 230 and the transmission of signals representing sensed ultrasound reflections from the anatomy.

Controller mount 330 comprises one or more structures supporting the printed circuit board or controller 232. Controller mount 330 is further configured to be connected are mounted to transducer assembly 300 to retain controller assembly 302 with respect to transducer assembly 300. In the example illustrated, controller mount 330 comprises a pair of ears 336 having apertures 338 which are aligned with apertures 324 in transducer support 314. Fasteners 332 extend through apertures 338 and through ears 336, through ears 322 and apertures 324 and into connection or securement with thermal drain 240.

Connectors 334 comprise plug or pin connectors mounted to the printed circuit board controller 302 for connection to connectors 318 of transducer assembly 300. In the example illustrated, controller assembly 302 includes a connector 334 on each face of the printed circuit board controller 232 for connection to a corresponding connector 318 extending from each of two flexible circuits 316 extending from transducer 230. In other implementations, other connection architectures and arrangements may be utilized.

Thermal drain 240 comprises one or more structures physically located between and in thermal contact with transducer 230 and casing wall 242, wherein the one or more structures of thermal drain 240 are formed from one or more materials having a thermal resistance less than a thermal resistance of the polymeric material forming casing wall 242. In one implementation, thermal drain 240 has a thermal conductivity of at least 150 watts per meter kelvin (W/(m·K)). In one implementation, thermal drain 240 comprises a metal, such as aluminum. In other implementations, thermal drain 240 may comprise other metals or other materials having thermal resistivity is less than that of the polymeric material of outer casing wall 242. In addition to structurally backing and strengthening casing wall 242 such that casing wall 242 may be formed with a reduced thickness, thermal drain 240 thermally conducts heat from transducer 230 outwardly away from transducer 230 towards casing wall 242 for enhanced heat dissipation from probe 220. Because heat is continuously and uniformly dissipated away from transducer 230 across thermal drain 240 and through the thinner casing wall 242, surface temperature regulations for the ultrasound probe may be more easily satisfied. As a result, additional energy may be directed into a patient's anatomy by probe 220 for enhanced image quality while still satisfying surface temperature regulations.

FIGS. 9-13 illustrate thermal drain 240 in more detail. FIGS. 14-19 illustrate thermal drain 240 with over molded outer casing wall 242. As shown by FIGS. 9-13, thermal drain 240 comprises a single integral unitary body formed from metal, such as aluminum. Thermal drain 240 comprises outer wall 350 and interior shelf 352. Outer wall 350 comprising ovular, frusto-conical shaped wall. Interior shelf 352 extends inwardly from outer wall 350 on opposite sides of thermal drain 240. Interior shelf 352 cooperates with outer wall 350 to form an opening 354 shaped and configured to receive lens 228 and transducer 230 such that sides of transducer 230 (or portions of transducer holder 322) are in close conformal contact with thermal drain 240. As shown by FIGS. 7 and 8, interior surfaces 356 of side walls 350 along opening 354 have a height extending from a lowering of transducer 230 to an upper end of transducer 230, effectively overlapping an entire side of transducer 230. Likewise, interior surfaces 358 of shelves 352 extend from a lower face of transducer 230 to beyond an upper face of transducer 230, effectively overlapping an entirety of the other sides of transducer 230. As a result, substantially an entirety of the outer side surfaces of transducer 230 contact and abut an opposite surface of thermal drain 240 for enhanced thermal conduction and heat dissipation. In other implementations, the shaping or configuration of opening 354, as well as the heights of interior surfaces 356, 358, may be varied depending upon the shaping or configuration of transducer 230 such that substantially an entirety of the side surfaces of transducer 230 are in contact with thermal drain 240.

In the example of limitation illustrated, shelves 352 to additionally include apertures or bores 362. Bores 362 are configured to receive fasteners 332. As shown by FIG. 7, shelves 352 of thermal drain 240 provide a mounting bracket or platform by which both controller assembly 302 and transducer assembly 300 may be secured to thermal drain 240 and nose 222. As a result, probe 228 be more easily assembled in less time and with fewer parts. In other implementations, thermal drain 240 may omit apertures 362, may be secured to transducer assembly 300 in other fashions, and may have other configurations.

Figure 14:
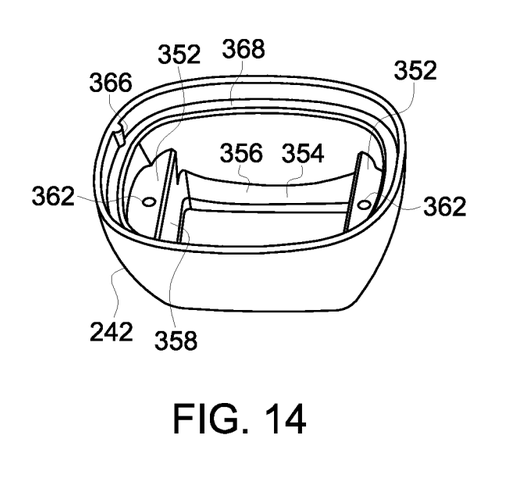
FIG. 14 is a top perspective view of the thermal drain of FIG. 4 with an example over molded outer casing wall.
Figure 15:
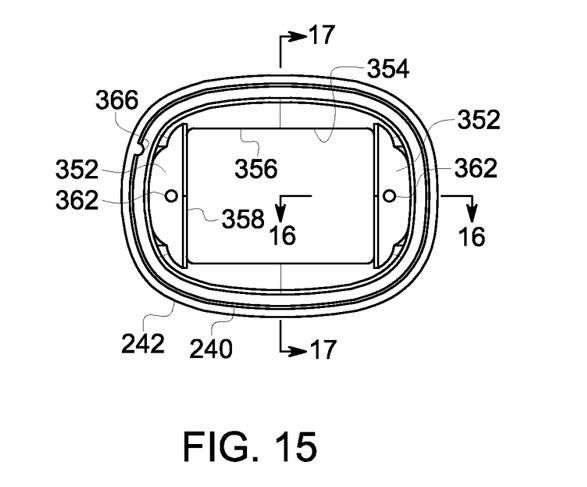
FIG. 15 is a top view of the thermal drain and casing wall of FIG. 14.

FIGS. 14-18 illustrate thermal drain 240 and casing wall 242 over molded against or about thermal drain 240. Such over molding facilitates greater surface area contact along an interface between drain 240 and wall 242 for enhanced thermal conduction from drain 240 to wall 242. As shown by FIGS. 14 and 15, wall 242 is integrally molded as a single unitary body of the polymeric material thus to form a post or projection 366 which projects over an upwardly facing rim 368 of thermal drain 240. Projection 366 retains or locks wall 242 with respect to thermal drain 240. In other implementations, other mechanisms may be used to lock or retain thermal drain 240 with respect to the over molded casing wall 242. For example, in other limitations, one of drain 240 and wall 242 may include a recess or detent while the other of drain 240 and wall 242 including projection extending into the recess or detent.

Figure 16:
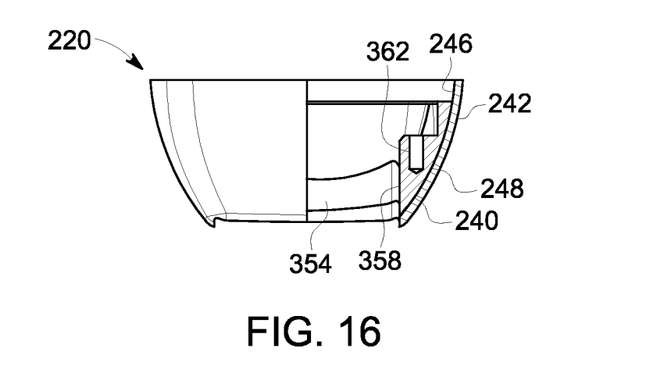
FIG. 16 is a partial sectional view of the thermal drain and casing wall of FIG. 15 taken along line 16-16.
Figure 17:
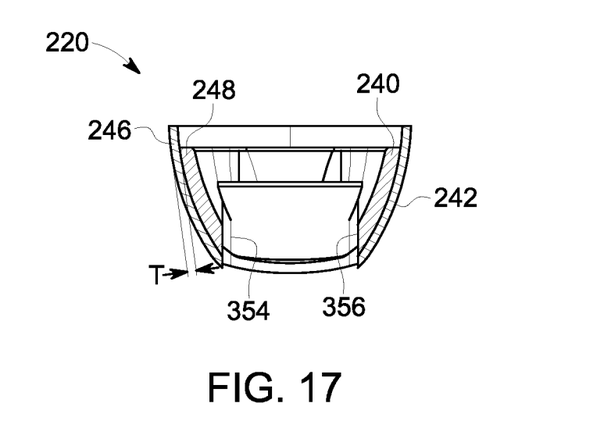
FIG. 17 is a sectional view of the thermal drain and casing wall of FIG. 15 taken along line 17-17.
Figure 18:
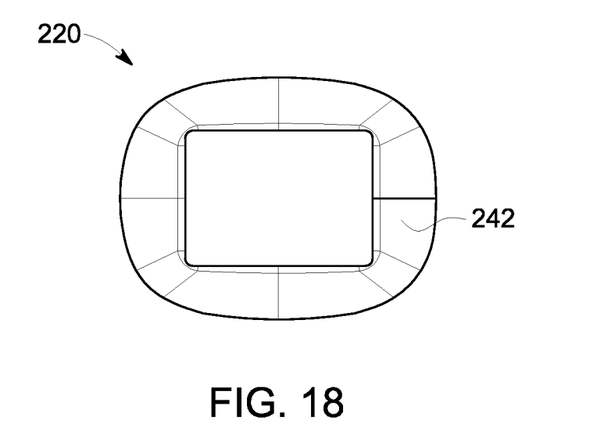
FIG. 18 is a bottom view of the thermal drain and casing wall of FIG. 14.
Figure 19:
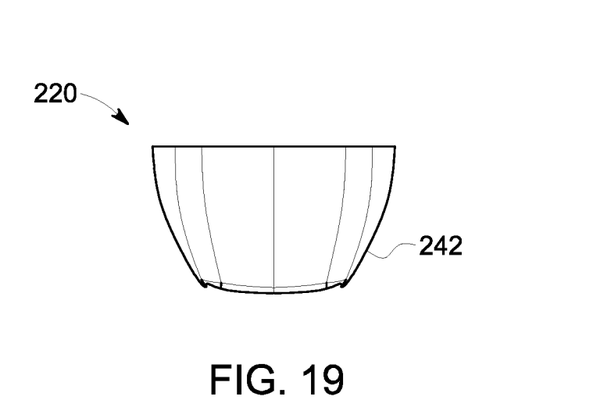
FIG. 19 is side view of the thermal drain and casing wall of FIG. 14.

As shown by FIGS. 16 and 17, wall 242 has an interior surface configuration 246 having a shape and size to identically match or substantially identically match an exterior surface configuration 248 of thermal drain 240 to provide an enhanced thermal interface between drain 240 and wall 246. As noted above, in the implementation illustrated, casing wall 242 has a thickness T of no greater than 3 mm and nominally less than 1 mm, preferably less than 0.6 mm, utilizing structural rigidity provided by thermal drain 240, yet providing probe 220 with a customary exterior appearance that satisfies ultrasound probe regulatory requirements for strength, durability and electrical isolation.

Figure 20:
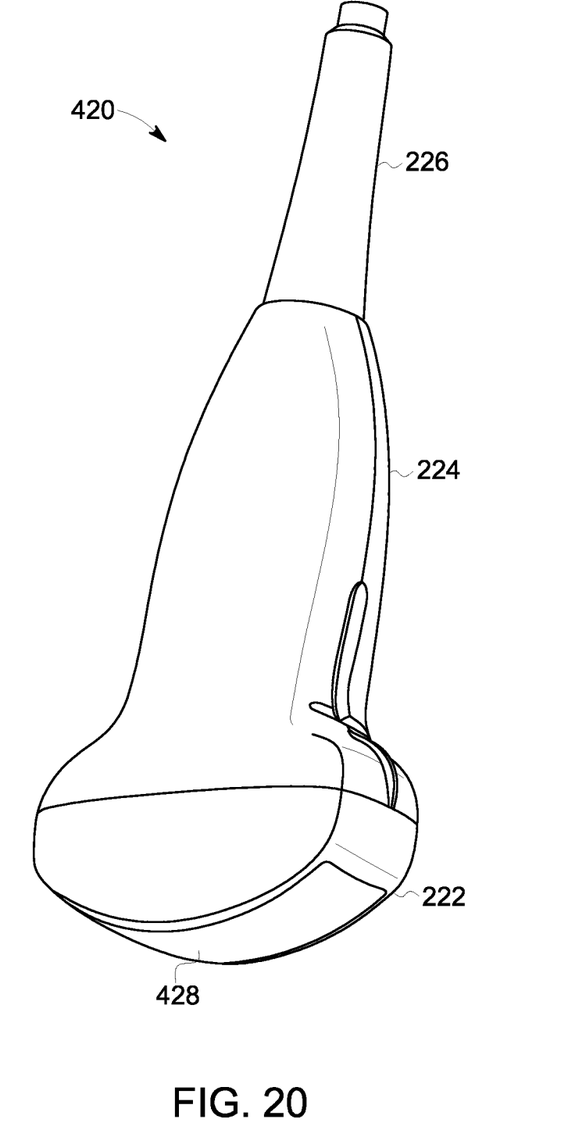
FIG. 20 is a perspective view of another example implementation of the ultrasound probe of FIG. 1.
Figure 21:
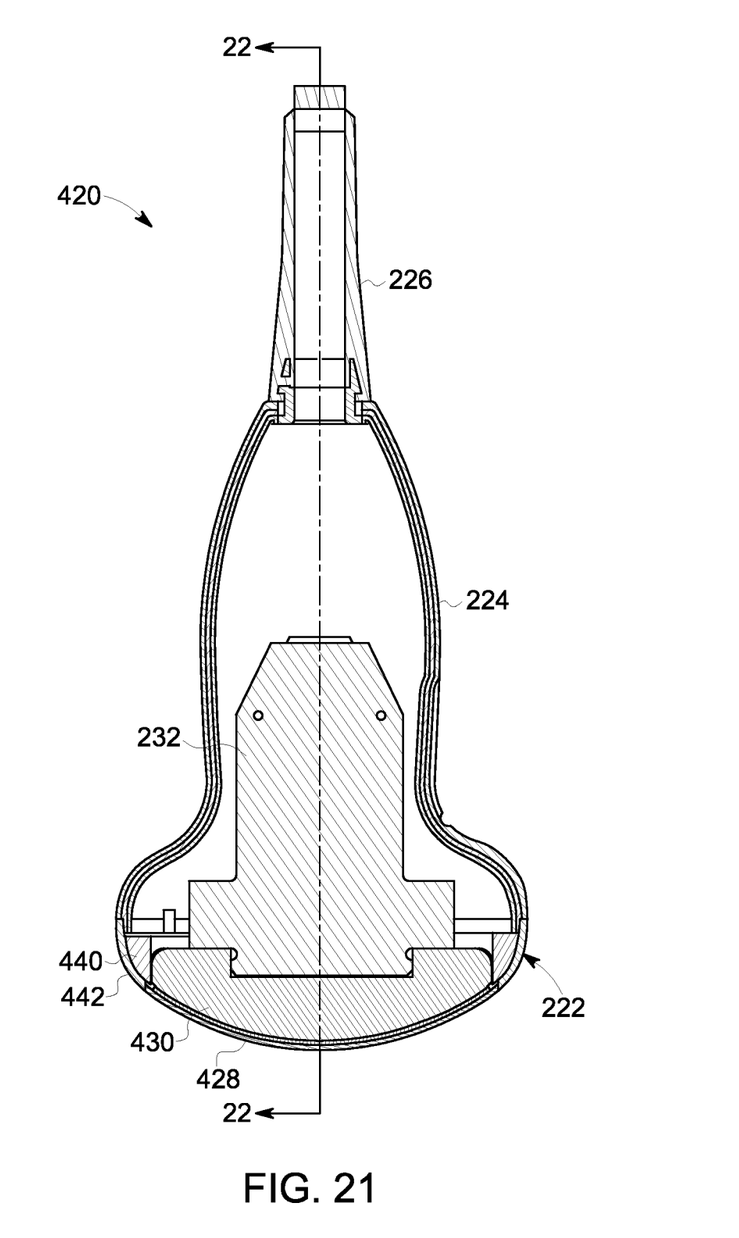
FIG. 21 is a sectional view of the ultrasound probe of FIG. 20.
Figure 22:
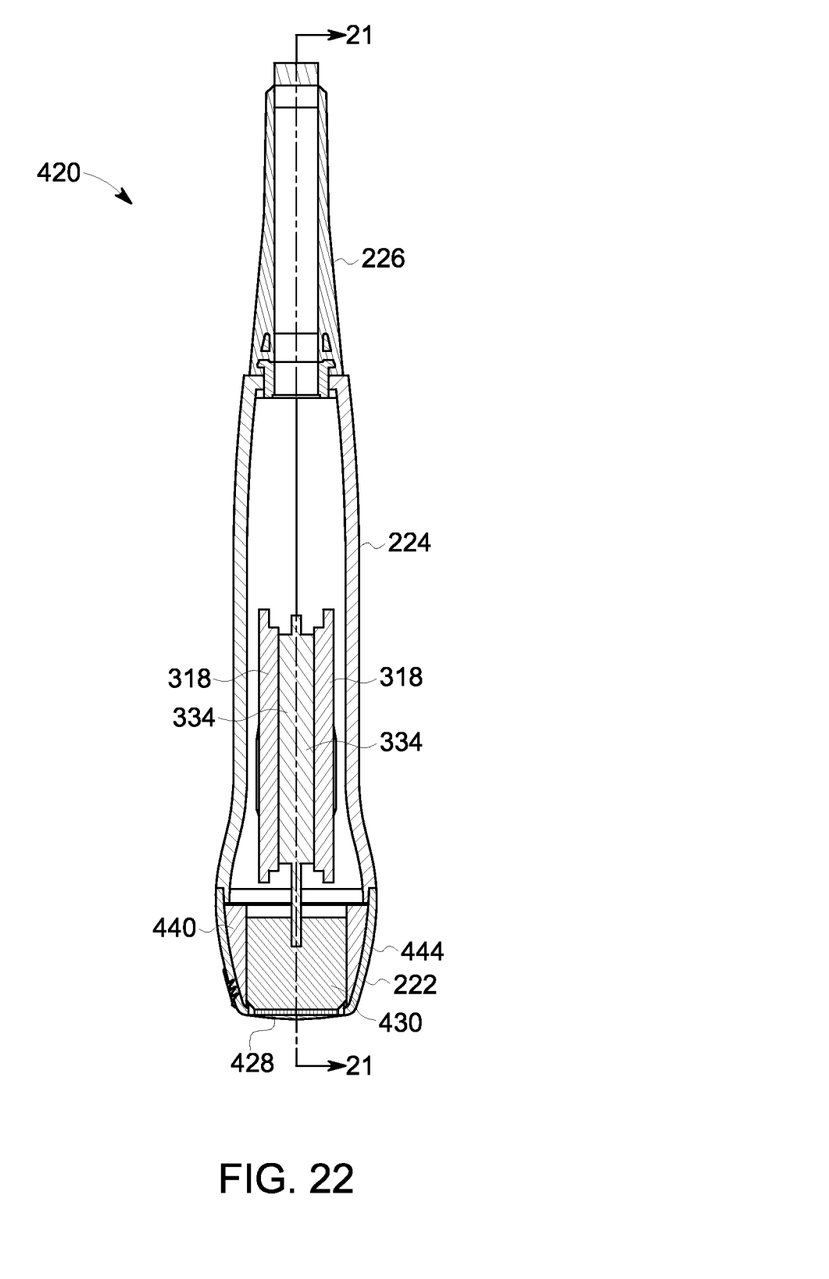
FIG. 22 is a sectional view of the ultrasound probe of FIG. 20 taken along line 22-22 of FIG. 21.

FIGS. 20-21 illustrate ultrasound probe 420, another example implementation of probe 20. Probe 420 is similar to probe 220 except that probe 420 is configured as an abdominal probe as compared to the phased array probe shown in FIG. 4. As shown by FIGS. 20-21, in contrast to probe 220, probe 420 includes a substantially curved lens 428 and a curved transducer 430 in place of lens 228 and transducer 230. Those remaining components of probe 422 correspond to components of probe 220 are numbered similarly.

As shown by FIGS. 20 and 21, probe 420 includes a thermal drain 440. As with thermal drain 240, thermal drain 440 comprises one or more structures physically located between and in thermal contact with transducer 430 and casing wall 442, wherein the one or more structures of thermal drain 440 are formed from one or more materials having a thermal resistance less than a thermal resistance of the polymeric material forming casing wall 442. In one implementation, thermal drain 440 has a thermal conductivity of at least 150 watts per meter kelvin (W/(m·K)). In one implementation, thermal drain 440 comprises a metal, such as aluminum. In other implementations, thermal drain 440 may comprise other metals or other materials having thermal resistivity is less than that of the polymeric material of outer casing wall 442. In addition to structurally backing and strengthening casing wall 442 such that casing wall 442 may be formed with a reduced thickness (less than or equal to 3 mm and nominally less than 1 mm, preferably less than 0.6 mm), thermal drain 440 thermally conducts heat from transducer 30 outwardly away from transducer 30 towards casing wall 442 for enhanced heat dissipation from probe 420. Because heat is continuously and uniformly dissipated away from transducer 430 across thermal drain 440 and through the thinner casing wall 442, surface temperature regulations for the ultrasound probe may be more easily satisfied. As a result, additional energy may be directed into a patient's anatomy by probe 420 for enhanced image quality while still satisfying surface temperature regulations.

In one implementation, thermal drain 440 comprises an insert positioned and held within casing wall 442 of nose 222. In another implementation, thermal drain 440 comprises a structure against which and about which casing wall 442 is over molded. Such over molding facilitates greater surface area contact along an interface between drain 440 and wall 442 for enhanced thermal conduction from drain 440 to wall 442. In one implementation, thermal drain 440 comprises an array of radial fins or baffles extending outwardly from transducer 430 to wall 442. In another implementation, thermal drain 440 comprises a substantially solid structure filling in all volume or space between transducer 430 and wall 442. In one implementation, wall 442 has an interior surface configuration 446 that has a shape and size to identically match or substantially identically match an exterior surface configuration 448 of thermal drain 440 to provide an enhanced thermal interface between drain 440 and wall 446.

Figure 23:
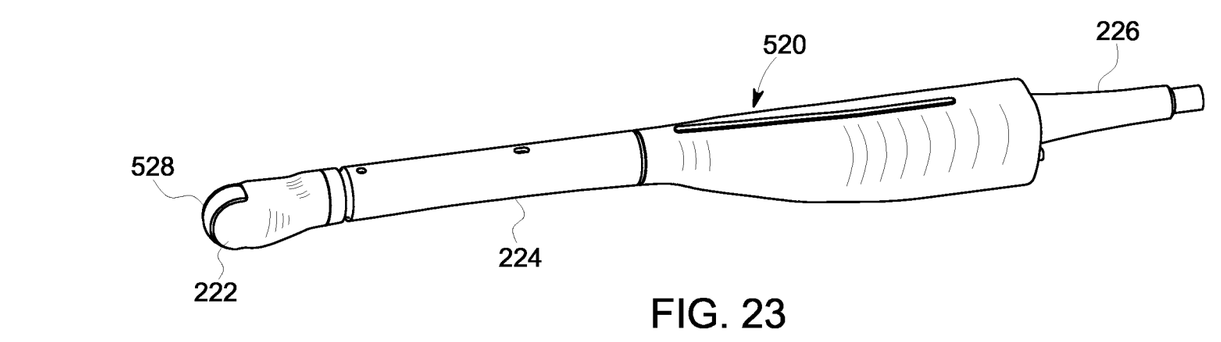
FIG. 23 is a perspective view of another example implementation of the ultrasound probe of FIG. 1.
Figure 24:
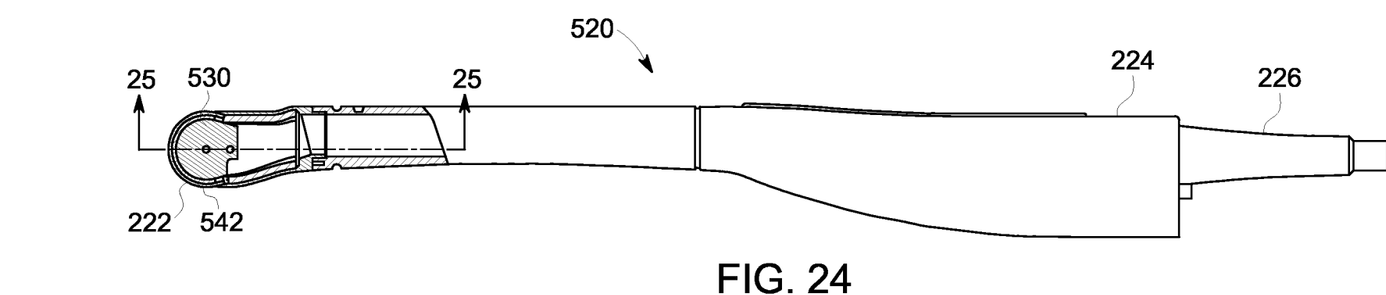
FIG. 24 is a sectional view of the ultrasound probe of FIG. 23.
Figure 25:
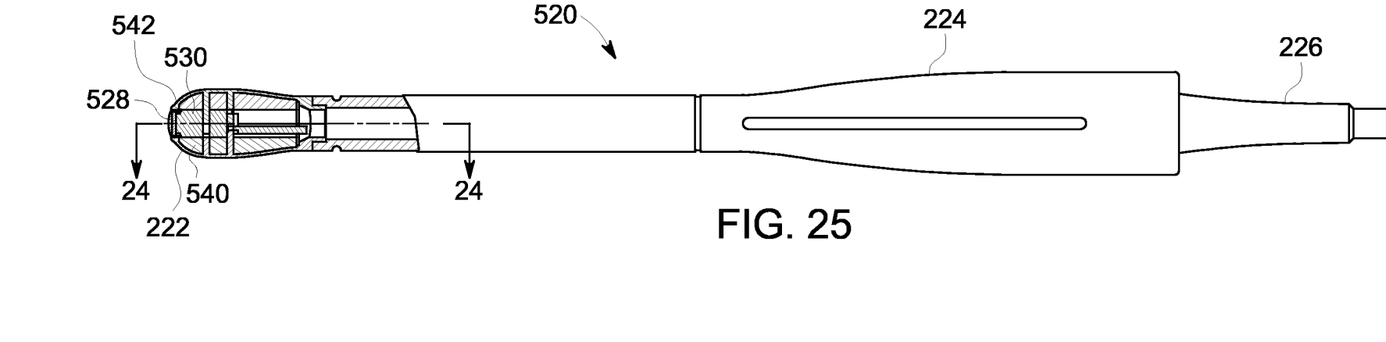
FIG. 25 is a sectional view of the ultrasound probe of FIG. 20 taken along line 25-25 of FIG. 24.

FIGS. 23-25 illustrate ultrasound probe 520, another example implementation of probe 20. Probe 520 is similar to probe 220 except that probe 520 is configured as an endocavity probe as compared to the phased array probe shown in FIG. 4. As shown by FIGS. 23-25, in contrast to probe 220, probe 520 includes a substantially curved (or rounded) lens 528 and a curved transducer 530 in place of lens 228 and transducer 230. Those remaining components of probe 520 that correspond to components of probe 220 are numbered similarly.

As shown by FIGS. 24 and 25, probe 520 includes a thermal drain 540. As with thermal drain 240, thermal drain 540 comprises one or more structures physically located between and in thermal contact with transducer 530 and casing wall 542, wherein the one or more structures of thermal drain 540 are formed from one or more materials having a thermal resistance less than a thermal resistance of the polymeric material forming casing wall 542. In one implementation, thermal drain 540 has a thermal conductivity of at least 150 watts per meter kelvin (W/(m·K)). In one implementation, thermal drain 540 comprises a metal, such as aluminum. In other implementations, thermal drain 540 may comprise other metals or other materials having thermal resistivity is less than that of the polymeric material of outer casing wall 542. In addition to structurally backing and strengthening casing wall 542 such that casing wall 542 may be formed with a reduced thickness (less than or equal to 3 mm and nominally less than 1 mm, preferably less than 0.6 mm), thermal drain 540 thermally conducts heat from transducer 530 outwardly away from transducer 530 towards casing wall 542 for enhanced heat dissipation from probe 520. Because heat is continuously and uniformly dissipated away from transducer 530 across thermal drain 540 and through the thinner casing wall 542, surface temperature regulations for the ultrasound probe may be more easily satisfied. As a result, additional energy may be directed into a patient's anatomy by probe 520 for enhanced image quality while still satisfying surface temperature regulations.

In one implementation, thermal drain 540 comprises an insert positioned and held within casing wall 542 of nose 522. In another implementation, thermal drain 540 comprises a structure against which and about which casing wall 542 is over molded. Such over molding facilitates greater surface area contact along an interface between drain 540 and wall 542 for enhanced thermal conduction from drain 540 to wall 542. In one implementation, thermal drain 540 comprises an array of radial fins or baffles extending outwardly from transducer 530 to wall 542. In another implementation, thermal drain 540 comprises a substantially solid structure filling in all volume or space between transducer 530 and wall 542. In one implementations, wall 542 has an interior surface configuration 546 that has a shape and size to identically match or substantially identically match an exterior surface configuration 548 of thermal drain 540 to provide an enhanced thermal interface between drain 540 and wall 546.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. An ultrasound probe comprising:
   a nose having an outer polymeric casing wall;
   a lens at an end of the nose;
   an ultrasound transducer within the nose behind the lens and
   a thermal drain thermally coupling the transducer to the casing wall, the thermal drain being formed from a material having a thermal resistance less than a thermal resistance of a material forming the casing wall.

2. The ultrasound probe of claim 1, wherein the casing wall has a thickness of less than or equal to 3 mm.

3. The ultrasound probe of claim 2, wherein the casing wall has a thickness of less than 1 mm.

4. The ultrasound probe of claim 3, wherein the casing wall has a thickness of less than 0.61 mm.

5. The ultrasound probe of claim 1, wherein the material of the thermal drain has a thermal conductivity of at least 150 watts per meter kelvin (W/(m·K)).

6. The ultrasound probe of claim 1, wherein the thermal drain is formed from a metal.

7. The ultrasound probe of claim 1, wherein the polymeric casing wall is overmolded about the thermal drain.

8. The ultrasound probe of claim 1, wherein the thermal drain comprises fastener openings receiving fasteners connected to the ultrasound transducer.

9. The ultrasound probe of claim 1, wherein the thermal drain completely surrounds sides of the ultrasound transducer.

10. The ultrasound probe of claim 1, wherein the outer polymeric casing wall has an interior surface configuration and wherein the thermal drain has an exterior surface configuration matching the interior surface configuration.

11. The ultrasound probe of claim 1, wherein the end of the nose is linear.

12. The ultrasound probe of claim 1, wherein the end of the nose is curved.

13. The ultrasound probe of claim 1, wherein the outer polymeric casing wall has an exterior surface having a frusto-conical shape.

14. A method comprising:
   generating ultrasonic vibrations in an ultrasound probe using an ultrasound transducer; and
   thermally conducting heat from the ultrasound transducer across a thermal drain to an outer polymeric casing of the ultrasound probe, wherein the thermal drain contacts and structurally supports the outer polymeric casing and wherein the outer polymeric casing has a casing wall with a thickness of less than or equal to 3 mm.

15. The method of claim 14, wherein the casing wall has a thickness of less than 1 mm.

16. The method of claim 14, wherein the thermal drain is formed from a material having a conductivity of at least 150 watts per meter kelvin (W/(m·K)).

17. The method of claim 14, wherein the thermal drain is formed from a metal.

18. The method of claim 14, further comprising:
forming the thermal drain;
over molding the outer polymeric casing about the thermal drain.

19. A method comprising:
forming a metallic thermal drain;
over molding an outer polymeric casing about the metallic thermal drain;
positioning an ultrasound probe transducer within the thermal drain.

20. The ultrasound probe of claim 1, wherein the thermal drain comprises a frustro-conical shaped wall extending 360° about all sides of the transducer.

\* \* \* \* \*